US008178588B2

(12) United States Patent  (10) Patent No.: US 8,178,588 B2
Young  (45) Date of Patent: *May 15, 2012

(54) METHOD AND APPARATUS FOR REDUCING $CO_2$ IN A STREAM BY CONVERSION TO A SYNGAS FOR PRODUCTION OF ENERGY

(75) Inventor: Gary C. Young, Cedar Rapids, IA (US)

(73) Assignee: GYCO, Inc., Cedar Rapids, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/070,586

(22) Filed: Mar. 24, 2011

(65) Prior Publication Data

US 2011/0172316 A1     Jul. 14, 2011

Related U.S. Application Data

(63) Continuation of application No. 11/956,107, filed on Dec. 13, 2007, now Pat. No. 7,923,476.

(51) Int. Cl.
*C07C 27/00* (2006.01)
(52) U.S. Cl. ............................................. 518/704
(58) Field of Classification Search .................. None
See application file for complete search history.

(56) References Cited

U.S. PATENT DOCUMENTS

| 4,166,786 | A | * | 9/1979 | Duraiswamy et al. | 208/410 |
| 4,752,623 | A | * | 6/1988 | Stevens et al. | 518/714 |
| 5,937,652 | A | * | 8/1999 | Abdelmalek | 60/648 |
| 2007/0254969 | A1 | | 11/2007 | Olah et al. | |
| 2009/0151252 | A1 | | 6/2009 | Young | |

OTHER PUBLICATIONS

Leal-Quiros, E., Plasma processing of municipal solid waste, Dec. 2004, Brazilian Journal of Physics, vo. 34, No. 4b pp. 1587-1593 (7 pages).*

Integrated Waste Management Board, Technology Evaluation and Economic Analysis of Waste Tire Pyrolysis, Gasificaton and Liquefication, Mar. 2006, University of California Riverside, Contractor's Report (103 pages).*

Choudhary, V.R. et al., Simultaneous steam and CO2 reforming of methane to syngas over NiO/MgO/SA-5205 in the presence and absence of oxygen, 1998, Applied Catalysis A: General, No. 168, pp. 33-46.*

Lemonidou, A.A. et al., Carbon dioxide reforming of methane over 5 wt% Ni/CaO-Al2-O3 catalyst, 2002, Applied Catalysis A: General, No. 228, pp. 227-235.*

Holt, N., "Gasification Process Selection—Trade-Offs and Ironies," Presented at the Gasification Technologies Conference 2004, Oct. 3-6, 2004, pp. 1-10, JW Marriott Hotel, Washington, DC.

(Continued)

*Primary Examiner* — Yate K Cutliff
(74) *Attorney, Agent, or Firm* — Slater & Matsil, L.L.P.

(57) ABSTRACT

A system and method for reducing the $CO_2$ in a gaseous stream, such as an exhaust stream, from a power plant or industrial plant, like a cement kiln, is disclosed. A preferred embodiment includes providing the gaseous stream to pyrolysis reactor along with a carbon source such as coke. The $CO_2$ and carbon are heated to about 1330° C. and at about one atmosphere with reactants such as steam such that a reaction takes place that produces syngas, carbon dioxide ($CO_2$) and hydrogen ($H_2$). The Syngas is then cleaned and provided to a Fischer-Tropsch synthesis reactor to produce Ethanol or Bio-catalytic synthesis reactor.

36 Claims, 5 Drawing Sheets

OTHER PUBLICATIONS

Rosenberg, W.G., et al., "Financing IGCC—3Party Covenant," BSCIA Working Paper Jan. 2004, Energy Technology Innovation Project, Belfer Center for Science and International Affairs, Feb. 2004, 143 pgs, John F. Kennedy School of Government, Harvard University, Cambridge, MA.

Stiegel, G.J., "Gasification—Versatile Solutions: Gasification Technologies Overview," NASEO 2006 Annual Meeting, Seattle, Washington, Sep. 10-13, 2006, 35 pgs., National Energy Technology Laboratory.

Van Bibber, L., et al., "Baseline Technical and Economic Assessment of a Commercial Scale Fischer-Tropsch Liquids Facility," DOE/NETL-2007/1260, Final Report, Apr. 9, 2007, 79 pgs.

Young, G. C., "How Trash Can Power Ethanol Plants," Public Utilities Fortnightly, Feb. 2007, pp. 72-74, 76.

Young, G. C., "Zapping MSW with Plasma Arc," Pollution Engineering, Nov. 2006, pp. 26-29.

ConocoPhillips, "E-Gas-Gasification," www.coptechnologysolutions.com/egas, ConocoPhillips Technology Solutions, Mar. 2004, 15 pgs.

URS Corporation, "Summary Report: Evaluation of Alternative Solid Waste Processing Technologies," Prepared for City of Los Angeles, Department of Public Works, Bureau of Sanitation, Sep. 2005, 40 pgs., Los Angeles, CA.

Roine, A., et al., "HSC Chemistry® v.5.0," Chemical Reaction and Equilibrium Software with Extensive Thermochemical Database Product Instruction Manual, Jun. 28, 2002, Chapters 11, 13 and 14, Outokumpu Research Oy.

Higman, C., et al., "Gasification: The Thermodynamics of Gasification," Second edition, 2008, Elsevier Publishing, 5 pages.

Young, G., "From Waste Solids to Fuel," Pollution Engineering Magazine, Feb. 2008, 4 pages.

L.-Q., E., "Plasma Processing of Municipal Solid Waste," Brazilian Journal of Physics, vol. 34, No. 4B, Dec. 2004, pp. 1587-1593.

"Technology Evaluation and Economic Analysis of Waste Tire Pyrolysis, Gasification and Liquefaction," Integrated Waste Management Board, Contractor's Report, Mar. 2006, University of California Riverside, 103 pages.

Supta, K. et al., "Carbon Dioxide Reforming with Methane in Low Temperature Plasmas," 2002, ACS, Fuel Chemistry Division Preprints, No. 47, vol. 1, pp. 269-272.

* cited by examiner

| FIG. 4A | FIG. 4B |

METHOD AND APPARATUS FOR REDUCING CO₂ IN A STREAM BY CONVERSION TO A SYNGAS FOR PRODUCTION OF ENERGY

This application is a continuation of U.S. patent application Ser. No. 11/956,107, entitled "Method and Apparatus for Reducing CO₂ in a Stream by Conversion to a Syngas for Production of Energy," filed on Dec. 13, 2007, now U.S. Pat. No. 7,923,476, which application is hereby incorporated herein by reference.

TECHNICAL FIELD

The present invention relates generally to the field of reducing the presence of carbon dioxide ($CO_2$), and in specific embodiments, to reducing the carbon dioxide in a gaseous exhaust stream from power plants and other types of industrial plants, and forming a Syngas ($CO+H_2$) that can, in turn, be used in the production of energy such as liquid fuels; for example, Ethanol.

BACKGROUND

Concern about global warming eventually leads to discussions about the need to reduce the amount of carbon dioxide that pours into the earth's atmosphere on a daily basis from power plants and other industrial factories. At the same time, concerns about dwindling supplies of fossil fuels have encouraged the development of liquid fuels such as Ethanol as future replacement fossil fuels. Unfortunately, most present methods of producing a liquid fuel such as Ethanol result in as much or more carbon dioxide being introduced into the atmosphere as does burning fossil fuels.

Therefore, a method for producing a Syngas, (easily convertible to Ethanol) from gaseous streams exhausted by industrial plants would offer many advantages in cost, as well as, an overall reduction in the carbon dioxide dumped into the atmosphere.

SUMMARY OF THE INVENTION

The present invention discloses methods and apparatus for reducing the carbon dioxide that is often present in gaseous streams exhausted or emitted from various power plants and types of industrial plants, such as a cement plant. For example, the typical gaseous exhaust stream of about 400,000 lbs/hr total from a cement plant will contain about 30%-40% (about 160,000 lbs/hr) of carbon dioxide ($CO_2$). However, instead of being exhausted to the atmosphere, according to the invention, this gaseous stream is provided to a reaction chamber, such as, for example, a pyrolysis chamber. Reactions take place in the pyrolysis chamber such that the gaseous stream is converted to contain Syngas ($CO+H_2$) and a reduced amount of carbon dioxide (i.e., about 75,195 lbs/hr). The reduction in carbon dioxide is about 53%, and the Syngas can then be cleaned and used as a feedstock for the production of Ethanol. For example, a bio-catalytic process such as a Fischer-Tropsch process could be used to produce the Ethanol.

More specifically, the process for reducing the carbon dioxide and forming the Syngas comprises maintaining a reaction chamber, such as a pyrolysis chamber, at a temperature of between about 400° C. and 5000° C. (typically between 400° C. and 2000° C.) and at a pressure of about one atmosphere or greater. Note, when using a Plasma Arc Gasification chamber, temperatures in the plasma arc zone can reach between 3000° C. and 7000° C. Heat is added as required since some desired reactions are endothermic. Although a pyrolysis chamber is used in a preferred embodiment, a conventional gasifier reactor, a gasification reactor or a plasma arc reactor is also believed to be suitable. A carbonaceous material such as coal, coke, solid waste, etc., is also provided to the reactor such that a Boudouard reaction (i.e. $C+CO_2 \leftrightarrow 2CO$) takes place.

BRIEF DESCRIPTION OF THE DRAWINGS

For a more complete understanding of the present invention, and the advantages thereof, reference is now made to the following descriptions taken in conjunction with the accompanying drawing, in which:

FIG. 4, which includes

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Figure 1:
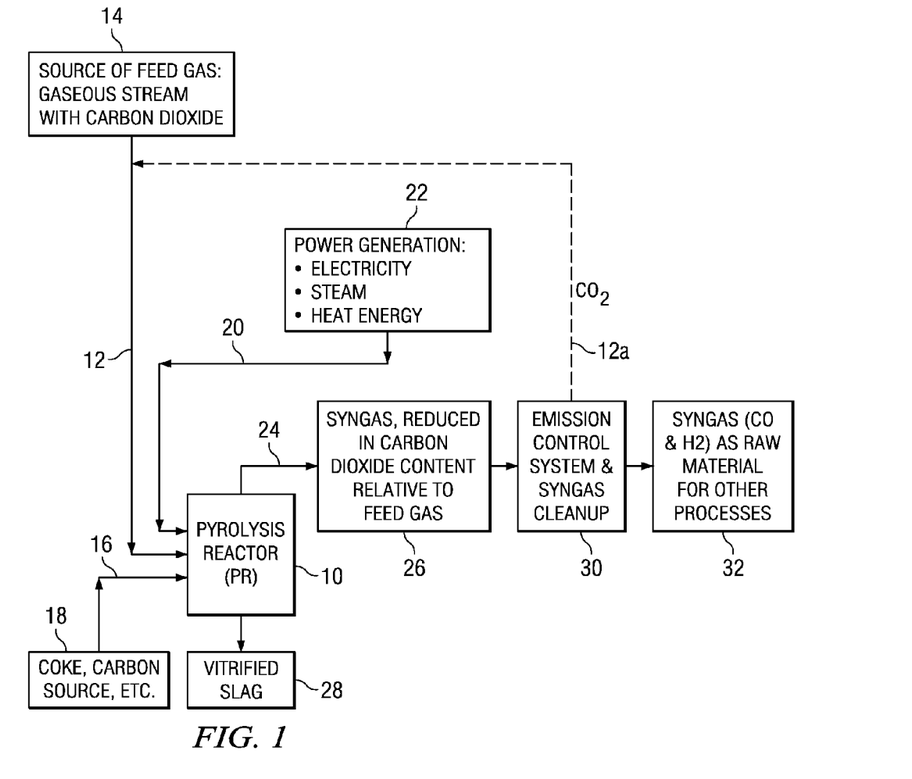
FIG. 1 is a block diagram illustrating the processes of the present invention.

Referring now to FIG. 1, there is illustrated a block diagram of the present inventive process. As shown, a reaction chamber 10 receives a gaseous stream or exhaust gases, as indicated by line 12, from a power plant or industrial plant 14 such as, for example only, a cement plant with a rotary kiln. The gaseous stream from a rotary kiln will typically comprise between about 55% to about 70% Nitrogen ($N_2$) and about 45% to about 30% carbon dioxide ($CO_2$) plus minute amounts of oxygen ($O_2$) and other impurities. The reaction chamber 10 is preferably a pyrolysis reactor, but could also include a conventional gasifier or a plasma arc gasifier. Also provided to reactor 10 is a carbonaceous material as indicated by line 16 such as coke, coal, or another hydrocarbon source 18, such as biomass materials or municipal solid waste. In addition, as will be appreciated by those skilled in the art, since a pyrolysis reaction (i.e. the thermal decomposition of organic material by heating in the absence of oxygen and other reagents, except possibly steam) takes place at a relatively high temperature. A source of heat energy 22, including electricity and/or steam, is provided as indicated at line 20.

The reaction in the pyrolysis chamber typically will take place at about one atmosphere or one bar and at a temperature of between about 400° C. and 2000° C., and preferably at about 1330° C. The primary chemical reaction that takes place in the pyrolysis reactor is the reaction of the carbonaceous material such as carbon (C) with carbon dioxide ($CO_2$) according to:

$$C+CO_2 \leftrightarrow 2CO, \qquad \text{Equation (1)}$$

which is also sometimes referred to as the Boudouard reaction.

Other reactions that may occur in the reaction chamber are:

$$C+H_2O \leftrightarrow CO+H_2,  \quad \text{Equation (2)}$$

often referred to as a gasification with steam;

$$CO+H_2O \leftrightarrow H_2+CO_2, \quad \text{Equation (3)}$$

referred to as a water-gas shift reaction; and $$C_nH_m+nH_2O \leftrightarrow nCO+(n+\tfrac{1}{2}m)H2, \quad \text{Equation (4)}$$

for steam reforming.

Importantly, as seen from Equation (1), the carbon (C) provided by the source 18 combines with one of the oxygen (O) atoms of the carbon dioxide ($CO_2$) molecules to form two molecules of carbon monoxide (2CO) which, of course, reduces the amount of carbon dioxide ($CO_2$) in the reaction chamber. In addition, as indicated by Equation (2), if water (i.e. steam) is available in the pyrolysis reactor, the carbon (C) will also react with the water ($H_2O$) to produce carbon monoxide and free hydrogen ($H_2$). It will also be appreciated that all of the carbon dioxide ($CO_2$) will not be converted to 2CO (i.e. carbon monoxide). Further, the steam ($H_2O$) may also react with some of the carbon monoxide (CO) to reform some carbon dioxide ($CO_2$) and some hydrogen ($H_2$) as indicated by Equation (3). Consequently, the pyrolysis reactor discharges Syngas as indicated on line 24 comprised of carbon monoxide (CO), hydrogen ($H_2$) a reduced amount of carbon dioxide ($CO_2$), as indicated by block 26. Also, as shown, there will typically be a vitrified slag or ash product 28 produced by the process depending upon the temperature of the pyrolysis reactor. The chemical content of the vitrified slag or ash will, of course, vary depending upon the carbonaceous source and temperature of the pyrolysis reactor.

The Syngas may then be provided to an emission control system 30 to remove impurities and clean up the Syngas. The Syngas control and cleanup system will remove impurities in the syngas from the pyrolysis reactor. Depending upon the feed to the pyrolysis reactor, the impurities in the syngas could be about 0.5 wt. % chlorine and 0.8 wt. % sulfur based upon an elemental analysis of the feed, as an example. Most of the sulfur is converted to hydrogen sulfide ($H_2S$) but some is converted to carbonyl sulfide (COS). Chlorine is converted to hydrogen chloride (HCl). Trace elements of mercury and arsenic can be found in the syngas prior to cleaning. Some particulate carryover occurs with the syngas from the pyrolysis reactor. Selection of the technology for gas cleanup depends upon depends upon the purity requirements of downstream processes using the syngas.

Particulate control is typically a Metal Candle filter or Water scrubber in combination with a cyclone. Sulfur recovery is typically a Claus plant. The acid gases such as hydrogen chloride are recovered by solvent-based processes such as Selexol or Rectisol.

Also as shown, the carbon dioxide ($CO_2$) in the Syngas is removed and may be returned to the pyrolysis reactor, as indicated by dotted line 12a. Thus, Syngas comprised of carbon monoxide (CO) and hydrogen ($H_2$) is available for further processing, as indicated at block 32.

Figure 4:
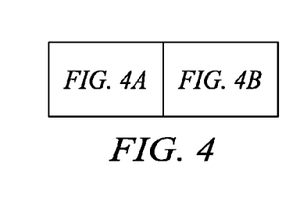
Figure 4A:
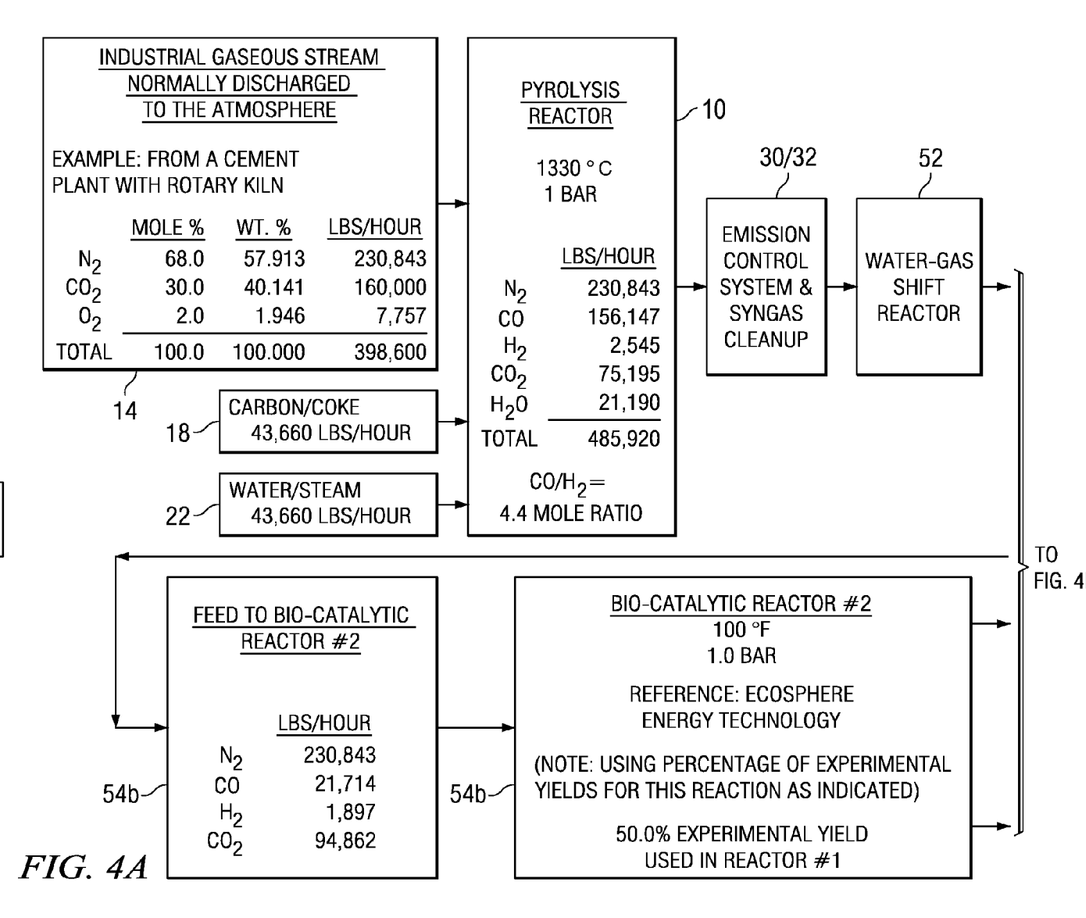
FIGS. 4a and 4b, is a detailed example of FIG. 3 illustrating the use of a first and a second bio-catalytic reactor.
Figure 4B:
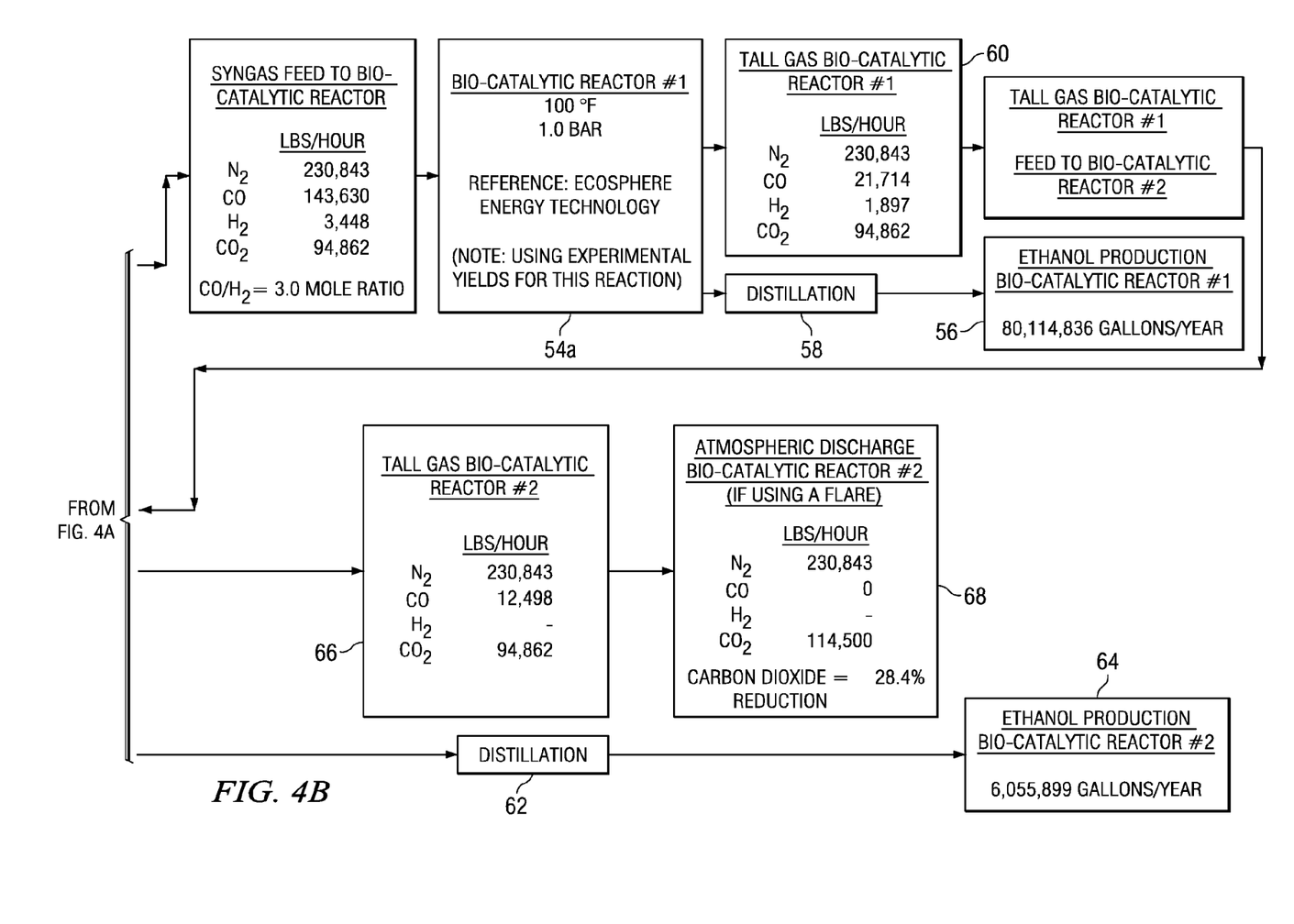

An example of the process of reducing the carbon dioxide in a gaseous stream from a power plant or rotary cement kiln is as follows:

In the embodiment shown in FIG. 4A, the total output gaseous stream from a rotary kiln of 398,600 lbs/hr is provided to a reactor 10, such as for example, a pyrolysis reactor. The total gaseous stream output includes about 160,000 lbs/hr (~40%) of carbon dioxide ($CO_2$). Also in the embodiment of FIG. 4A, a carbonaceous source of about 43,663 lbs/hr of coke or coal (C) and a similar amount of steam ($H_2O$) is provided. The temperature of the reactor is maintained at about 1330° C. and at about one atmosphere (one bar) of pressure. The output of the pyrolysis reactor will be a raw or uncleaned Syngas comprised of about 156,147 lbs/hr of carbon monoxide (CO); 2,545 lbs/hr of hydrogen ($H_2$) and about 75,195 lbs/hr of carbon dioxide ($CO_2$). Also, as is clearly shown in the embodiment of FIG. 4A, none of the 43,660 lbs/hr of carbonaceous material 18 (carbon/coke) provided to the reactor 10 remains in the reactor 10 as carbonaceous material (C). However, as is also shown, about 21,190 lbs/hr of the 43,660 lbs/hr of the water/steam ($H_2O$) remains unused in the reactor 10 of FIG. 4A (i.e., does not react). Likewise, the 230,843 lbs/hr of nitrogen ($N_2$) that was in the gaseous stream 14 also remains unused. Thus, it is seen that at this stage of the process the carbon dioxide ($CO_2$) has been reduced by about 53%. As is well known, the input mass to the reactor must, of course, equal the mass output from the reactor. The inputs and outputs of reactor 10 shown in FIG. 4A. are clearly equal. Specifically, the mass input equals 485,920 lbs/hr and comprises 230,843 lbs/hr of $N_2$+160,000 lbs/hr of $CO_2$+7,757 lbs/hr of $O_2$+43,660 lbs/hr of Carbon/Coke+43,660 lbs/hr of Water/Steam. Likewise, the mass output also equals 485,920 lbs/hr and comprises 230,843 lbs/hr $N_2$+156,147 lbs/hr of CO+2,545 lbs/hr $H_2$+75,195 lbs/hr of $CO_2$+21,190 lbs/hr of $H_2O$. Also note, the Oxygen ($O_2$) has been depleted to zero by the reactions in the reactor 10 as noted in FIG. 4A. In addition, the carbon monoxide (CO) in the Syngas provides a significant economic advantage, since as will be discussed later; some bio-catalytic processes effectively use carbon monoxide (CO) as feed stock for organisms in bioreactors that produce Ethanol.

Figure 2:
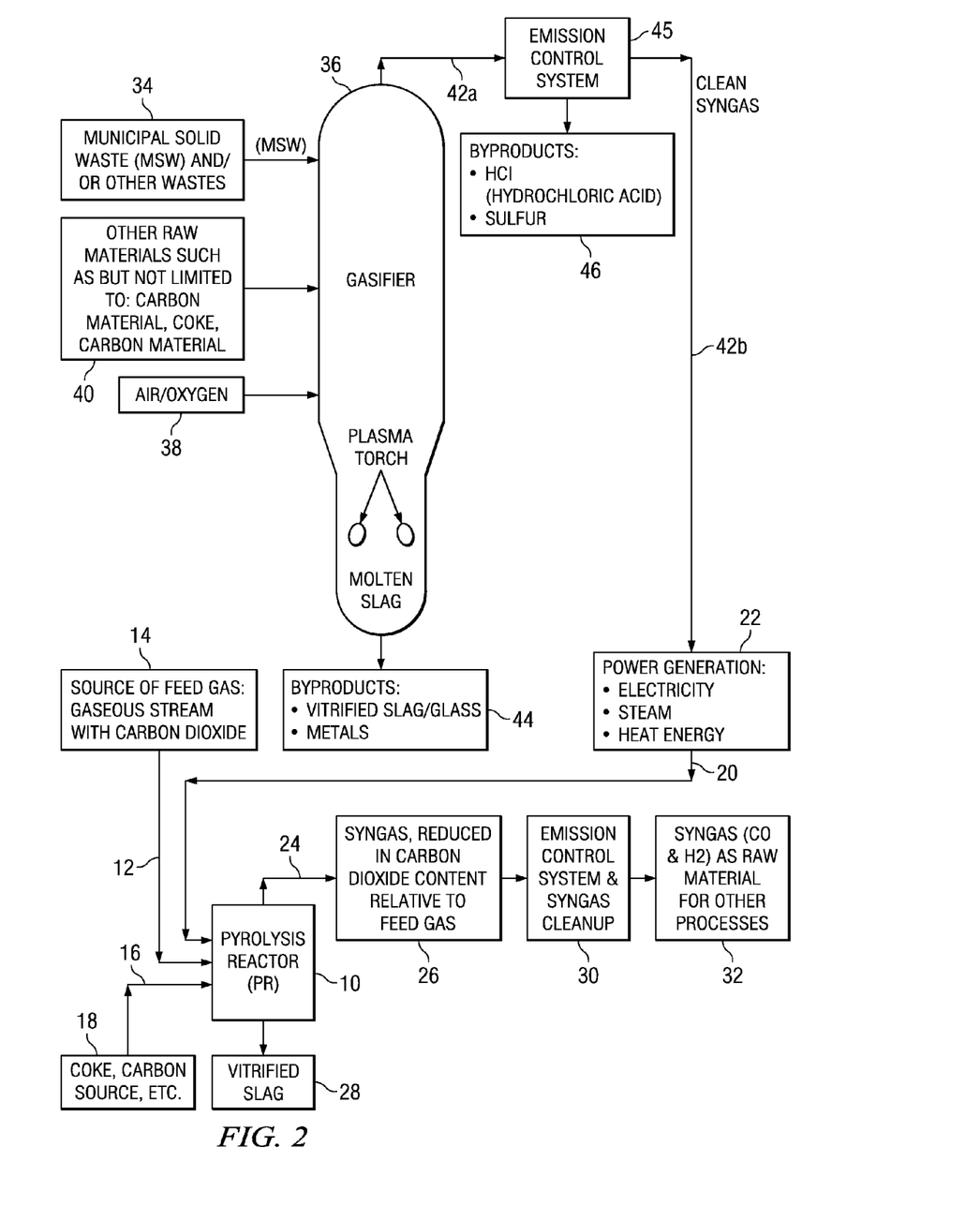
FIG. 2 is similar to FIG. 1, but includes an available process for converting municipal solid waste to Syngas that, in turn, uses the Syngas to provide the necessary power (e.g. electricity, steam and/or heat) to the pyrolysis reactor of the present invention.

As will be appreciated by those skilled in the art, other known ecologically friendly processes can be combined with the inventive process described above. As an example and referring to FIG. 2, there is shown the process of, FIG. 1 wherein the source 22 of electricity, steam or heat energy is the product of a plasma arc gasification process that uses various waste products such as municipal solid waste (MSW) as a fuel source. As shown, the MSW 34 is provided to the plasma arc gasifier 36 along with an oxygen source 38 and a carbon material 40 such as coke provide a dirty or raw Syngas as indicated by line 42a. Other byproducts 44 include metals and vitrified slag. The dirty Syngas is then provided to an emission control system 45 to remove various other byproducts 46 from the Syngas such as sulfur and hydrochloric acid, etc. This leaves a clean Syngas provided on line 42b that is then used to provide the required steam and heat energy used by the pyrolysis reactor 10.

Figure 3:
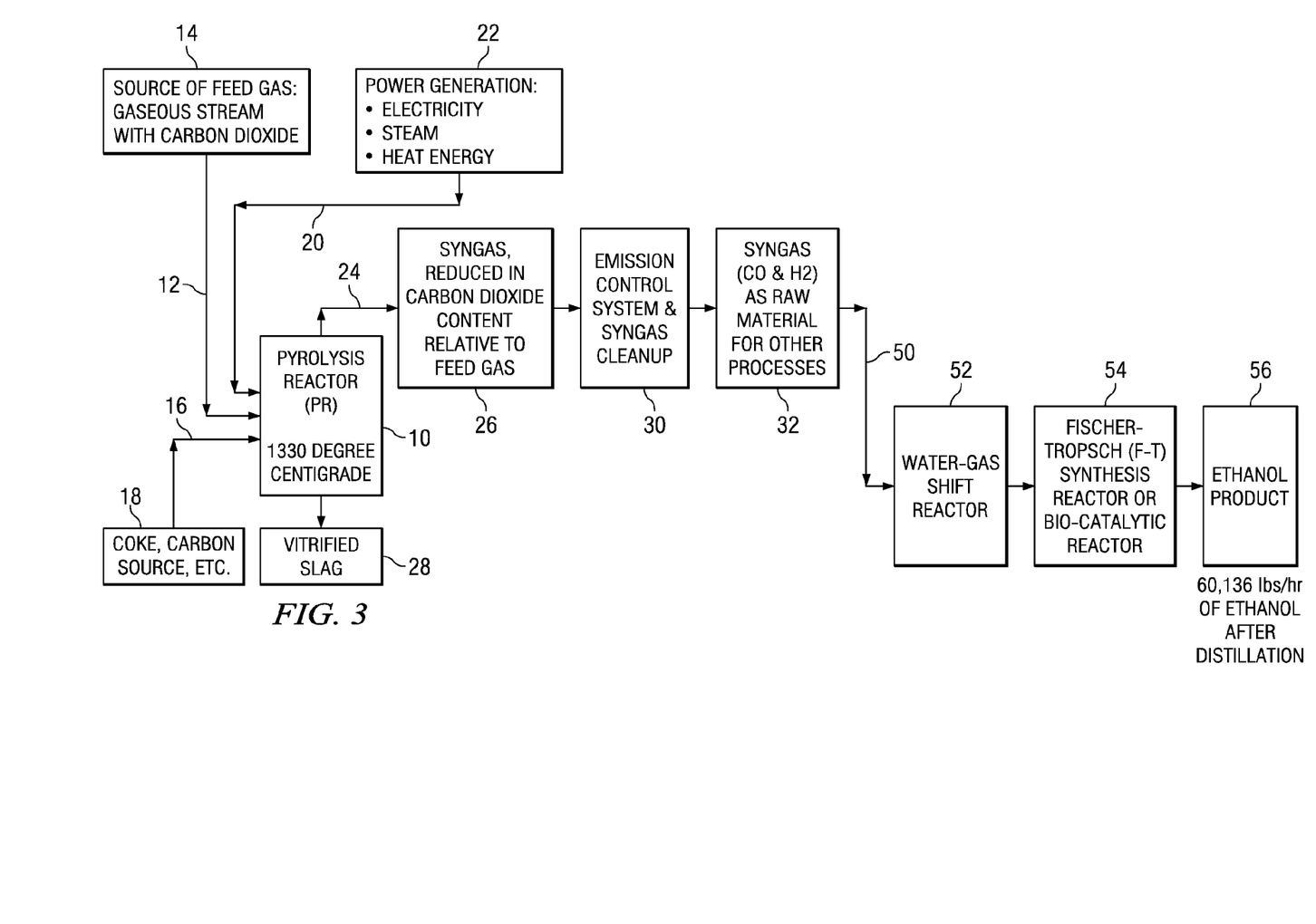
FIG. 3 illustrates the process of FIG. 1 or 2 combined with another process for the production of Ethanol.

Referring now to FIG. 3, there is again shown the process of FIG. 1. However, as shown, the produced Syngas is now further processed to provide Ethanol. As shown, the Syngas 32 is provided by line 50 to a water-gas shift reactor 52 and then to a bio-catalytic reactor 54 such as a Fischer-Tropsch synthesis reactor. As known by those skilled in the art, the Fischer-Tropsch reactor may be used to convert the Syngas to Ethanol 56. More specifically, assuming that a flow of Syngas comprised of about 156,147 lbs/hr of carbon monoxide (CO), 2,545 lbs/hr of hydrogen ($H_2$), 75,105 lbs/hr of carbon dioxide $CO_2$) is provided to the water-gas shift reactor 52, about 8,051 lbs/hr of water (steam) will be required to adjust the carbon monoxide (CO) and hydrogen ($H_2$) molar ratio to 3.00 moles of carbon monoxide (CO) for 1.00 each mole of hydrogen ($H_2$). This adjustment is according to the reaction represented by:

$$CO + H_2O \rightarrow CO_2 + H_2.$$ Equation (5)

More specifically, a mass flow rate of 156,147 lbs/hr of carbon monoxide (CO) is 5,574.7 lbmole/hr, and 2.545 lbs/hr of hydrogen ($H_2$) is 1,262.4 lbmole/hr of hydrogen ($H_2$). Therefore, the water-gas shift reactor is set to shift or rearrange the amount of carbon monoxide (CO) and hydrogen ($H_2$) such that the final mixture ratio comprises 5,127.8 lbmole/hr of carbon monoxide (CO) and 1,709.3 lbmole/hr of hydrogen ($H_2$). This shift is selected to facilitate the reaction that produces Ethanol ($C_2H_5OH$). The reaction is shown below in Equation (6).

$$CO + H_2 + H_2O \rightarrow C_2H_5OH.$$ Equation (6)

Similar to the above discussion concerning Equation (5), this reaction takes place with a carbon monoxide (CO) to hydrogen ($H_2$) molar ratio of between 3.0 and 0.2 of Carbon Monoxide to 1.0 of hydrogen. With this adjustment, the production of Ethanol at 100% of its actual experimental yield from a bio-catalytic reactor is 60,136 lbs/hr of Ethanol, which is about 80,120,000 gallons/yr after distillation.

This reaction does not produce carbon dioxide ($CO_2$). Therefore, from the start of the industrial gaseous stream 14 containing 160,000 lbs/hr of carbon dioxide ($CO_2$) to the discharge of the pyrolysis reactor 10, the reduction in emitted carbon dioxide ($CO_2$) is 75,105 lbs/hr, or a reduction of about 53%. The water-gas shift adds about 19,667 lbs/hr of carbon dioxide ($CO_2$) for a total of 94,862 lbs/hr of carbon dioxide ($CO_2$) rather than the original 160,000 lbs/hr for about a total 40% reduction. Of course, in addition to the reduction in exhausted $CO_2$, there is a bonus of 60,136 lbs/hr (or 80,120,000 gallons/yr) of Ethanol.

Referring to FIG. 4, there is shown a more detailed block flow diagram for producing Ethanol that uses two bio-catalytic reactors in series and which illustrates the flow rate of gases, steam, and carbonaceous materials, etc. The reference numbers of common elements or systems are the same as in FIG. 3. However, as shown, rather than a single bio-catalytic converter 54, there is a first bio-catalytic converter 54a that results in the 80,114,836 gallons/yr of Ethanol (block 56) after being distilled as indicated at 58. As is also shown, however, the tail gas from the bio-catalytic converter 54a comprises 94,862 lbs/hr of carbon dioxide ($CO_2$), as well as 21,714 lbs/hr of carbon monoxide (CO) and 1,897 lbs/hr of hydrogen ($H_2$) as indicated in block 60. Therefore, according to this embodiment, the tail gas of block 60 is provided to a second bio-catalytic converter 54b, that is assumed to operate at a 50% yield rather than 100%. Another water-gas shift, as discussed above, is also indicated. The output of the second bio-catalytic converter 54b is another 6,055,899 gallons/yr of Ethanol, as indicated at block 64, after passing the gas through a second distillation process 62 for a total of 86,170,735 gallons/yr. Since the process does not add carbon dioxide ($CO_2$), the tail gas indicated at block 66 from the second bioreactor 54b still contains the 94,802 lbs/hr. of carbon dioxide ($CO_2$) but reduced carbon monoxide (CO). However, if we assume the discharge of the tail gas from the second reactor to the atmosphere is accomplished with a flare burn-off, an additional 19,638 lbs/hr of carbon dioxide ($CO_2$) may be added to the 94,862 lbs/hr. to give a total of 114,500 lbs/hr of carbon dioxide ($CO_2$). This still represents a 28.4% reduction of carbon dioxide ($CO_2$) plus the bonus of 86,170,735 gallons/yr of Ethanol.

Although the present invention and its advantages have been described in detail, it should be understood that various changes, substitutions and alterations can be made herein without departing from the spirit and scope of the invention as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A process for producing syngas that reduces the amount of carbon dioxide in a gaseous stream, the process comprising:
    maintaining a reaction chamber at a temperature of between 400° C. and 5000° C. and at a pressure of about one bar or greater;
    providing a carbonaceous material selected from the group consisting essentially of coal, coke, solid waste and biomass material to said reaction chamber;
    providing $H_2O$ to said reaction chamber;
    introducing a gaseous stream containing carbon dioxide ($CO_2$) to said reaction chamber;
    reacting materials in said reaction chamber, wherein the reacting materials consisting essentially of said carbonaceous material, said $H_2O$ and said carbon dioxide ($CO_2$) from said gaseous stream to reduce said $CO_2$ and to form syngas comprising carbon monoxide (CO) and hydrogen ($H_2$), said reacting step further resulting in none of the provided carbonaceous material remaining as un-reacted carbonaceous material in said reaction chamber or said syngas; and
    discharging said formed syngas.

2. The process of claim 1, wherein said reaction chamber is selected to be one of a pyrolysis reactor, a conventional gasifier or a plasma arc gasifier.

3. The process of claim 1, wherein said reaction chamber is a pyrolysis reactor.

4. The process of claim 1, wherein said $H_2O$ is provided as a reactant into said reaction chamber as steam.

5. The process of claim 1, wherein a Boudouard reaction comprises said step of reacting.

6. The process of claim 1, further comprising the step of providing said carbon monoxide (CO) and hydrogen ($H_2$) (i.e. syngas) to an emission control system to clean said syngas by removing impurities.

7. The process of claim 6, wherein said cleaned syngas is provided to a water-gas shift reactor to adjust the carbon monoxide and hydrogen molar ratio between 0.20 to 3.00 molecules of carbon monoxide for 1.00 molecules of hydrogen.

8. The process of claim 7, wherein said molar adjusted carbon monoxide and hydrogen are provided to a bio-catalytic reactor to produce Ethanol.

9. The process of claim 8, wherein said bio-catalytic reactor is a Fischer-Tropsch synthesis reactor.

10. The process of claim 7, wherein an output of said bio-catalytic reactor is provided to another bio-catalytic reactor to provide additional Ethanol.

11. The process of claim 1, wherein said syngas comprising carbon monoxide and hydrogen is provided to a bio-catalytic reactor to produce Ethanol.

12. The process of claim 6, wherein said cleaned syngas is provided to a water-gas shift reactor to adjust the carbon monoxide and hydrogen molar ratio.

13. The process of claim 12, wherein said molar adjusted carbon monoxide and hydrogen are provided to a bio-catalytic reactor to produce Ethanol.

14. The process of claim 13, wherein said bio-catalytic reactor is a Fischer-Tropsch synthesis reactor.

15. The process of claim 13, wherein an output of said bio-catalytic reactor is provided to another bio-catalytic reactor to provide additional Ethanol.

16. The process of claim 1 wherein said reacting step results in a portion of the $H_2O$ remaining in the reactor.

17. The process of claim 1 wherein the reaction chamber is maintained at a temperature of between 1,330° C. and 5,000° C.

18. The process of claim 1, wherein the reaction chamber is maintained at a temperature of between 400° C. and 2000° C.

19. The process of claim 1 wherein no particulate carbonaceous material remains as un-reacted carbonaceous material.

20. The process of claim 1, wherein the amount of $CO_2$ in said formed gas is at least 28.4% less than the amount of $CO_2$ in the input gaseous stream.

21. The process of claim 1, wherein the amount of $CO_2$ in said formed gas is at least 53% less than the amount of $CO_2$ in the input gaseous stream.

22. A process for producing syngas that reduces the amount of carbon dioxide in a gaseous stream, the process comprising:
    maintaining a reaction chamber at a temperature of between 400° C. and 5000° C. and at a pressure of about one bar or greater;
    providing materials to said reaction chamber comprising a carbonaceous material selected from the group consisting essentially of coal, coke solid waste and biomass material, $H_2O$, and a gaseous stream that includes carbon dioxide ($CO_2$);
    reacting said materials provided to said reaction chamber, the reacting materials consisting essentially of said carbonaceous material, said $H_2O$ and said provided carbon dioxide ($CO_2$) to reduce said $CO_2$ to form syngas in said reaction chamber comprising carbon monoxide (CO), hydrogen ($H_2$), and an amount of $CO_2$ that is less than the amount of $CO_2$ that was provided in said gaseous stream; and
    discharging said formed syngas.

23. The process of claim 22 wherein no particulate carbonaceous material remains as un-reacted carbonaceous material.

24. The process of claim 22 wherein the reaction chamber is maintained at a temperature of between 1,330° C. and 5,000° C.

25. The process of claim 22 wherein said reacting step consumes said carbonaceous material such that none of the carbonaceous material remains as un-reacted carbonaceous material in said syngas.

26. The process of claim 25, wherein none of the carbonaceous material remains as un-reacted carbonaceous material in said reaction chamber.

27. The process of claim 22, wherein said reaction chamber is selected to be one of a pyrolysis reactor, a conventional gasifier or a plasma arc gasifier.

28. The process of claim 22, wherein said $H_2O$ is provided as steam in said reaction chamber.

29. The process of claim 22, further comprising the step of providing said carbon monoxide (CO) and hydrogen ($H_2$) (i.e. syngas) to an emission control system to clean said syngas by removing impurities.

30. The process of claim 29, wherein said cleaned syngas is provided to a water-gas shift reactor to adjust the carbon monoxide and hydrogen molar ratio between 0.20 to 3.00 molecules of carbon monoxide for 1.00 molecules of hydrogen.

31. The process of claim 30, wherein said molar adjusted carbon monoxide and hydrogen are provided to a bio-catalytic reactor to produce Ethanol.

32. The process of claim 22 wherein said reacting step results in a portion of the $H_2O$ remaining in the reactor.

33. The process of claim 22, wherein the amount of $CO_2$ in said formed gas is at least 28.4% less than the amount of $CO_2$ in the input gaseous stream.

34. The process of claim 22, wherein the amount of $CO_2$ in said formed gas is at least 53% less than the amount of $CO_2$ in the input gaseous stream.

35. A process for producing syngas that reduces the amount of carbon dioxide in a gaseous stream, the process comprising:
    maintaining a reaction chamber at a temperature of between 1,330° C. and 5000° C. and at a pressure of about one bar or greater;
    providing a carbonaceous material to said reaction chamber, said carbonaceous material selected from the group consisting essentially of coal, coke, solid waste and biomass material;
    providing $H_2O$ to said reaction chamber;
    introducing a gaseous stream containing carbon dioxide ($CO_2$) to said reaction chamber; and
    reacting materials in said reaction chamber, the reacting materials consisting essentially of carbonaceous material, $H_2O$ and carbon dioxide ($CO_2$) to reduce said $CO_2$ to form syngas, said formed syngas comprising carbon monoxide (CO), hydrogen ($H_2$) and a reduced amount of $CO_2$, said provided carbonaceous material, said provided $H_2O$ and said carbon dioxide ($CO_2$) reacting such that the carbonaceous material is fully consumed and none remains as un-reacted carbonaceous material in said formed syngas; and
    discharging said formed syngas.

36. The process of claim 35 wherein no particulate carbonaceous material remains as un-reacted carbonaceous material.

* * * * *